(12) United States Patent
Hoelzle et al.

(10) Patent No.: US 11,642,835 B2
(45) Date of Patent: May 9, 2023

(54) ADDITIVE MANUFACTURING METHODS UTILIZING A ROBOTIC ARM

(71) Applicant: OHIO STATE INNOVATION FOUNDATION, Columbus, OH (US)

(72) Inventors: David J. Hoelzle, Columbus, OH (US); Desmond M. D'Souza, Columbus, OH (US); Andrej Simeunovic, Columbus, OH (US); Ali Asghari Adib, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 17/600,950

(22) PCT Filed: Apr. 3, 2020

(86) PCT No.: PCT/US2020/026616
§ 371 (c)(1),
(2) Date: Oct. 1, 2021

(87) PCT Pub. No.: WO2020/206283
PCT Pub. Date: Oct. 8, 2020

(65) Prior Publication Data
US 2022/0097292 A1    Mar. 31, 2022

Related U.S. Application Data

(60) Provisional application No. 62/829,137, filed on Apr. 4, 2019.

(51) Int. Cl.
*B29C 64/118* (2017.01)
*B33Y 10/00* (2015.01)
(Continued)

(52) U.S. Cl.
CPC ............ *B29C 64/118* (2017.08); *B33Y 10/00* (2014.12); *C12N 5/0062* (2013.01); *B29K 2105/0061* (2013.01); *B29L 2031/753* (2013.01)

(58) Field of Classification Search
None
See application file for complete search history.

(56) References Cited

U.S. PATENT DOCUMENTS 10,117,968 B2    11/2018    Gladman
2007/0128279 A1*  6/2007    Edgren ................. A61P 29/00
                                                    514/629
(Continued)

OTHER PUBLICATIONS

International Search Report for related International Application No. PCT/US2020/026616; report dated Oct. 8, 2020; (2 pages).
(Continued)

*Primary Examiner* — Mohammad M Ameen
(74) *Attorney, Agent, or Firm* — K&L Gates LLP

(57) ABSTRACT

The present disclosure provides methods for freeform extrusion-based additive manufacturing via a robotic arm. In specific aspects, methods are particularly provided for minimally invasive, intracorporeal three-dimensional printing of biocompatible materials. An end effector of a robotic arm includes a sharp member and a reservoir filled with a printing material. The provided method may include piercing a substrate with the sharp member. A bulb or microbolus of material may be extruded beneath the substrate surface to act as an anchor. The end effector may be manipulated to extrude biomaterial along a printing path. Periodically along the printing path, the sharp member is used to pierce the substrate surface create additional respective anchors. In some instances, the method may terminate after extruding material to form a single layer construct. In other instances,
(Continued)

the method includes forming one or more layers on top of the initial base layer anchored to the substrate.

20 Claims, 8 Drawing Sheets

(51) Int. Cl.
*C12N 5/00* (2006.01)
*B29K 105/00* (2006.01)
*B29L 31/00* (2006.01)

(56) References Cited

U.S. PATENT DOCUMENTS

| | | |
|---|---|---|
| 2015/0105891 A1 | 4/2015 | Golway et al. |
| 2016/0288414 A1* | 10/2016 | Ozbolat ................. A61F 2/2875 |
| 2017/0198252 A1 | 7/2017 | Gladkaya et al. |
| 2017/0217088 A1* | 8/2017 | Boyd, IV .............. B29C 64/209 |
| 2017/0325932 A1* | 11/2017 | Hoelzle ............... A61F 2/30756 |
| 2018/0207863 A1* | 7/2018 | Porter .................... B29C 64/129 |
| 2018/0296343 A1* | 10/2018 | Wei ....................... B29C 64/241 |

OTHER PUBLICATIONS

Written Opinion for related International Application No. PCT/US2020/026616; report dated Oct. 8, 2020; (5 pages).

* cited by examiner

ADDITIVE MANUFACTURING METHODS UTILIZING A ROBOTIC ARM

PRIORITY CLAIM

The present application is a National Phase of International Application No. PCT/US2020/026616, filed Apr. 3, 2020, which claims priority to and the benefit of U.S. Provisional Application 62/829,137, filed Apr. 4, 2019. The entire contents of each are incorporated herein by reference and relied upon.

STATEMENT OF GOVERNMENT RIGHTS

This invention was made with government support under grant/contract numbers 1708819 and 1343012 awarded by the National Science Foundation. The government has certain rights in the invention.

This invention was made with government support under Sponsor Award No. 1708819, Project No. 60059476, awarded by the National Science Foundation Division of Civil, Mechanical, and Manufacturing Innovation, and Sponsor Award No. 1343012, awarded by the National Science Foundation Division of Graduate Education and Research Development. The government has certain rights in the invention.

BACKGROUND

Patients with diseased or damaged tissue typically have such diseased or damaged tissue repaired by either autologous grafting (from the patients themselves), allogenic grafting (from cadavers or donors), or via implantation of bio-inert structural meshes and fixtures. Autologous and allogenic grafts, however, are in short supply and require either two surgical sites or a donor. Structural meshes and fixtures, on the other hand, are mechanically and biologically mismatched to native tissue. For instance, such bio-inert structural meshes and fixtures cannot remodel or repair for the sake of longevity, nor can they grow in size for pediatric patients.

Tissue engineering is a field that applies the principles of biology and engineering to the development of functional substitutes for damaged tissue. The aim of tissue engineering is to regenerate natural tissue function without the need for autologous grafting, allogenic grafting, xenograft, or for the implantation of bio-inert structures. Tissue engineering constructs are typically composed of (i) a scaffold (3D porous construct to replicate the natural extracellular matrix), (ii) tethered or free growth factors, drugs, and cells, and (iii) fixation mechanisms. Growth factors, drugs, and cells are often collectively termed biologics.

Tissue engineering constructs may be created using additive manufacturing ("AM"), also known as 3D printing, which is a process that creates a physical object from a digital design by additively forming the object layer-by-layer. One example of AM is extrusion-based AM, which includes extruding a material from a nozzle onto a platform to build an object layer by layer. In some processes, the platform adjusts vertically while the nozzle adjusts horizontally. In other processes, the nozzle may be adjusted three-dimensionally while the platform remains stationary. Advances have also been made to three-dimensionally print material on curved or uneven surfaces using robotic arms.

Ideally, tissue engineering constructs either stimulate or permit de novo growth in culture (in vitro or ex vivo) or in patients themselves (in vivo) during the initial healing phase and then slowly degrade as de novo tissue restores natural function. Tissue engineering constructs range from being architecturally simple, such as microboluses with encapsulated cells or foamed scaffolds saturated in BMP-2 growth factor, to incredibly complex, with multiple domains of different mechanical properties, chemistries, and bioactivities. Typically, tissue engineering may be successful for simpler flat, tubular, and hollow architectures in humans and animal models. Complex, solid tissue engineering, however, is still an open problem because of the challenges of vascularization and replication of structural and biological inhomogeneity. Additionally, tissue engineering constructs for tissue repair are typically printed in a lab and require an open, invasive surgery to be implanted in a patient. Open, invasive surgery increases the morbidity associated with the implantation procedure.

Various minimally invasive procedures exists that do not require opening a patient up to the extent of an open, invasive surgery and thus reduce the morbidity associated with the procedure. Such minimally invasive procedures include a wide variety of laparoscopic and endoscopic procedures performed through keyhole incision sites. Robotic surgery instruments, such as the Da Vinci surgical system marketed and sold by Intuitive Surgical, enable surgeons to perform robotic minimally invasive procedures that improve upon regular minimally invasive surgery by providing a surgeon with more articulation or dexterity inside a patient's body while reducing hand tremors and providing other advantages. Robotic surgery instruments can therefore enable procedures that are more complicated or make procedures easier and/or safer. Additionally, minimally invasive procedures (regular or robotic) reduce operating room time for procedures as compared to open, invasive surgery. Typical robotic surgery instruments, however, cannot create three-dimensional structures using AM. Further, typical robotic surgery instruments cannot intracorporeally create three-dimensional structures using AM.

Intracorporeal tissue engineering is the fabrication of tissue engineering constructs inside the body. Fabricating tissue engineering constructs inside the body requires a material that is bio-compatible and that can be printed in the intracorporeal environment. Natural and synthetic hydrogel materials are one typical class of materials for use in tissue engineering. Hydrogels can be printed using AM, are compatible with encapsulated cells, and can be composed with growth factors and drugs. The chemical and physical properties of hydrogels are additionally readily tuned via hydrogel chemistry design. Typically, hydrogel materials are crosslinked—transition from liquid to solid gel—via chemical or ultraviolet ("UV") light exposure. The intracorporeal environment, however, does not permit chemical or UV crosslinking. For instance, excess crosslinking initiator via chemical crosslinking may cause an immune reaction. UV light exposure is feasible; however, high UV exposure doses to a patient may induce DNA damage and tissue aging.

Accordingly, there exists a need for minimally invasive methods of intracorporeal three-dimensional printing of biocompatible materials.

BRIEF SUMMARY OF THE INVENTION

The present disclosure provides new and innovative methods for additive manufacturing using an end effector of an actuator joint mechanically linked to a robotic arm.

In light of the disclosures herein, and without limiting the scope of the invention in any way, in a first aspect of the present disclosure, which may be combined with any other aspect listed herein unless specified otherwise, a method for additive manufacturing using an end effector of an actuator joint mechanically linked to a robotic arm, the end effector including a sharp member, includes piercing a printing surface at a first anchor point with the sharp member. A first bulb of printing material is extruded beneath the printing surface at the first anchor point. The first bulb of printing material is solidified. Printing material is then extruded along a first printing path on the printing surface. The printing material along the first printing path is solidified. The printing surface is pierced at a second anchor point with the sharp member. A second bulb of printing material is extruded beneath the printing surface at the second anchor point. The second bulb is solidified. Printing material is then extruded along a second printing path on the printing surface. The printing material along the second printing path is solidified. The printing surface is pierced at a third anchor point with the sharp member. A third bulb of printing material is extruded beneath the printing surface at a third anchor point. The third bulb is then solidified.

In a second aspect of the present disclosure, which may be combined with any other aspect listed herein unless specified otherwise, extruding respective printing material and solidifying the respective printing material are simultaneous.

In a third aspect of the present disclosure, which may be combined with any other aspect listed herein unless specified otherwise, the printing material partially solidifies as it is extruded.

In a fourth aspect of the present disclosure, which may be combined with any other aspect listed herein unless specified otherwise, solidifying the printing material includes exposing the printing material to light.

In a fifth aspect of the present disclosure, which may be combined with any other aspect listed herein unless specified otherwise, the printing surface is continuously exposed to the light while the printing material is extruded.

In a sixth aspect of the present disclosure, which may be combined with any other aspect listed herein unless specified otherwise, the lights has a wavelength in the visible spectrum.

In a seventh aspect of the present disclosure, which may be combined with any other aspect listed herein unless specified otherwise, the light has a wavelength between 400 nm and 496 nm.

In an eighth aspect of the present disclosure, which may be combined with any other aspect listed herein unless specified otherwise, the printing surface is human or animal tissue.

In a ninth aspect of the present disclosure, which may be combined with any other aspect listed herein unless specified otherwise, the printing surface is intracorporeal.

In a tenth aspect of the present disclosure, which may be combined with any other aspect listed herein unless specified otherwise, the printing material is a hydrogel.

In an eleventh aspect of the present disclosure, which may be combined with any other aspect listed herein unless specified otherwise, the hydrogrel includes 7% gelatin methacryloyl, 3% laponite, and 3% methylcellulose.

In a twelfth aspect of the present disclosure, which may be combined with any other aspect listed herein unless specified otherwise, a method for additive manufacturing using an end effector of an actuator joint mechanically linked to a robotic arm, the end effector including a sharp member, includes extruding printing material along a first printing path on a printing surface to create a first material layer. The first printing path includes a plurality of anchor points. Creating the first material layer includes: (1) piercing the printing surface at each respective anchor point with the sharp member, (2) extruding a respective bulb of printing material beneath the printing surface at each respective anchor point, and (3) solidifying each of the respective bulbs of printing material. The first material layer is also solidified. Printing material is then extruded along a second printing path on the first material layer to create a second material layer. The second material layer is solidified. Printing material is then extruded along a third printing path on the second material layer to create a third material layer. The third material layer is solidified.

In a thirteenth aspect of the present disclosure, which may be combined with any other aspect listed herein unless specified otherwise, for example the twelfth aspect, the method further includes repeatedly creating a plurality of material layers by extruding printing material along a printing path on each directly preceding layer.

In a fourteenth aspect of the present disclosure, which may be combined with any other aspect listed herein unless specified otherwise, at least one of the material layers of the plurality of material layers includes a material different than the other material layers.

In a fifteenth aspect of the present disclosure, which may be combined with any other aspect listed herein unless specified otherwise, the material layers are created in a crisscrossing pattern with respect to adjacent material layers.

In a sixteenth aspect of the present disclosure, which may be combined with any other aspect listed herein unless specified otherwise, a method for the delivery of targeted molecules using an end effector of an actuator joint mechanically linked to a robotic arm, the end effector including a sharp member, includes piercing a surface at a first target site with the sharp member. A first bulb of a biomaterial is extruded beneath the surface at the first target site. The biomaterial includes the targeted molecules. The first bulb of biomaterial is solidified. The surface is then pierced at a second target site different than the first target site with the sharp member. A second bulb of the biomaterial is extruded beneath the surface at the second target site. The second bulb of biomaterial is solidified. Targeted molecules are eluted from each of the first bulb and the second bulb of the biomaterial.

In a seventeenth aspect of the present disclosure, which may be combined with any other aspect listed herein unless specified otherwise, the targeted molecules include at least one selected from the group consisting of tethered growth factors, cells, drugs, radioactive agents, and radiographic contrast agents.

In an eighteenth aspect of the present disclosure, which may be combined with any other aspect listed herein unless specified otherwise, for example the sixteenth aspect, the method further includes translating the end effector from the first target site to the second target site prior to piercing the surface at the second target site.

In a nineteenth aspect of the present disclosure, which may be combined with any other aspect listed herein unless specified otherwise, each of the first bulb and the second bulb includes a portion of biomaterial that extends above the surface.

In a twentieth aspect of the present disclosure, which may be combined with any other aspect listed herein unless specified otherwise, for example the sixteenth aspect, the method further includes repeatedly piercing the surface at a plurality of target sites with the sharp member, extruding a respective bulb of the biomaterial at each respective target site, and solidifying each respective bulb of the biomaterial.

DETAILED DESCRIPTION

Figure 1A:
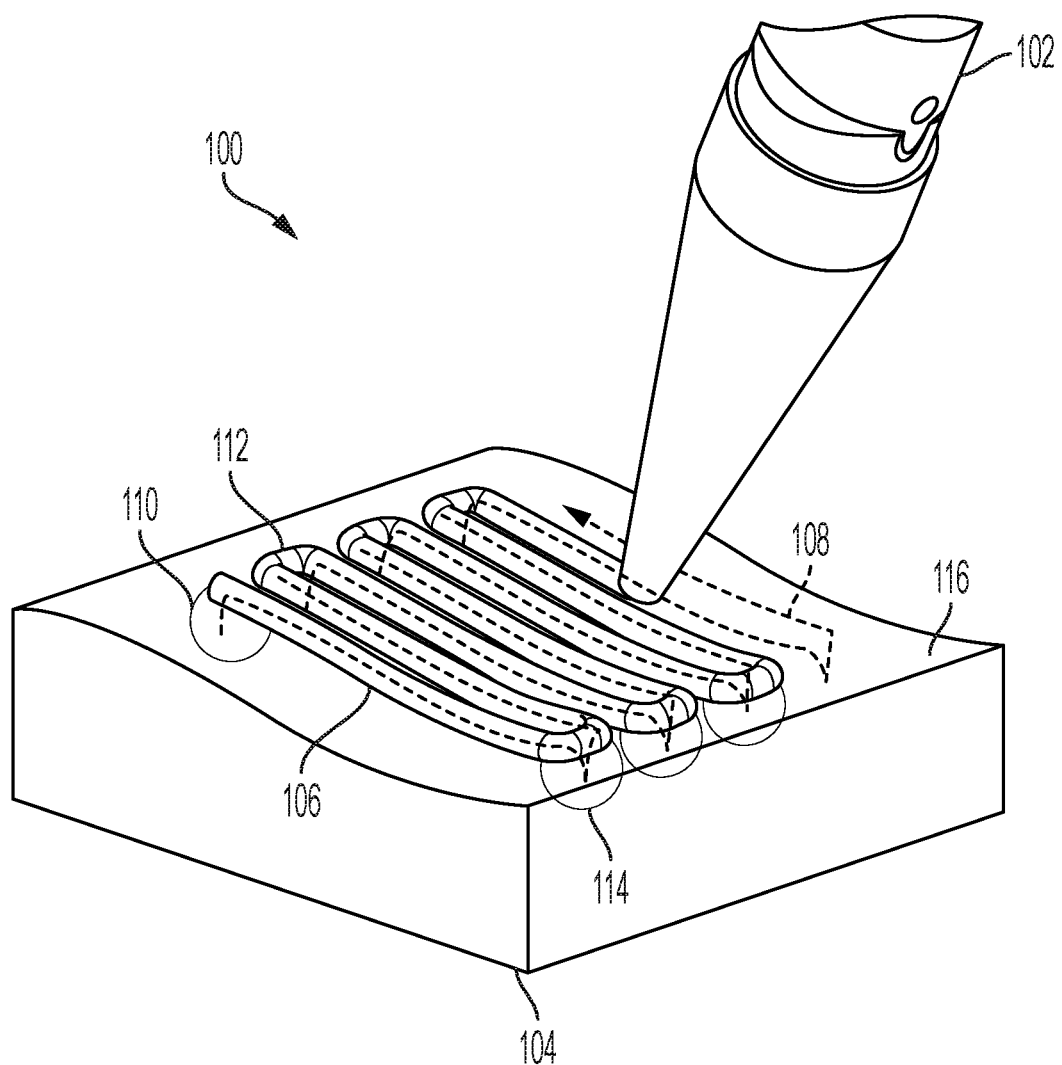
FIG. 1A illustrates an example printing method, according to an aspect of the present disclosure.

The present disclosure provides new and innovate methods for freeform extrusion-based additive manufacturing ("AM") via a robotic arm. The provided method enables three-dimensionally printing material within a volume through a small hole. In specific aspects, the present disclosure particularly provides new and innovative methods for minimally invasive, intracorporeal three-dimensional printing of biocompatible materials. Typically, tissue engineering constructs for intracorporeal tissue repair are printed in a lab and require an open, invasive surgery to be implanted in a patient. Open, invasive surgery increases the morbidity associated with the implantation procedure. The provided methods conversely enable tissue engineering constructs to be three-dimensionally printed intracorporeally through "keyhole" incisions. The provided methods therefore offer the benefits of tissue engineering to patients without the morbidity associated with open, invasive surgeries.

An end effector of an actuator joint mechanically linked to a robotic arm includes a reservoir filled with a printing material, such as a biomaterial. For example, the robotic arm may be a component of a robotic surgery instrument. The end effector also includes a sharp member from which the printing material may be extruded. The provided method may include making a "keyhole" incision in a patient with a cannula, and inserting the end effector's sharp member through the incision to access a target area to extrude a tissue engineering construct. For example, the target area may be a particular soft tissue of the patient. The provided method may then include piercing the patient's soft tissue with the end effector's sharp member. A bulb or micro-bolus of biomaterial may be extruded beneath the soft tissue surface in order to act as an anchor that maintains the final tissue construct in position. For instance, the bulb or micro-bolus of material is larger than the pierced hole created in the soft tissue surface by the sharp member.

The end effector may then be manipulated to extrude biomaterial along a printing path. Periodically along the printing path, the end effector's sharp member is used to pierce the soft tissue surface in order to extrude another bulb or micro-bolus anchor. In some instances, the method may terminate after extruding biomaterial to form a single layer construct. In other instances, the method includes forming one or more biomaterial layers on top of the initial base layer anchored to the patient's soft tissue. For example, the provided method may include extruding biomaterial to create a mesh construct. In another example, the provided method may include extruding biomaterial to create tubular or membrane-like tissue structures or other 3D constructs.

In one example, the provided method may include delivering targeted molecules to a patient. In such an example, the method includes piercing the patient's soft tissue and extruding a bulb or micro-bolus of biomaterial that includes targeted molecules. The patient's soft tissue may be pierced, and a bulb or micro-bolus of biomaterial extruded, and one or more target sites. The biomaterial then elutes the targets molecules. The biomaterials used in the printing methods described above may also include targeted molecules in some instances.

In other aspects of the present disclosure, the provided method includes freeform extrusion-based additive manufacturing ("AM") via a robotic arm for non-body applications. For example, injection molding manufacturing procedures may be used to manufacture parts that include complex internal geometries, such as automotive or aerospace parts. In such examples, the machining of the inside of the mold is complicated and difficult to fabricate. The provided method may ease the fabrication process by enabling three-dimensional printing of the mold's internal features within a hollow shell through a small hole. In other instances, the provided method may enable three-dimensional printing within a volume through a small hole for other suitable and similar non-body applications.

As used herein, "minimally invasive" refers to surgery, such as endoscopic surgery, that can be accomplished with several small incisions in order to gain access to a surgical site. "Minimally invasive" can refer to endoscopy, laparoscopy, arthroscopy, endovascular, keyhole, and like types of surgery. Common to all of these procedures, a surgeon will visualize a worksite within the human body using a camera, and pass surgical instruments through small incisions (or natural orifices) to the worksite. Minimally invasive surgery enables the surgeon to manipulate tissues and organs in a manner which avoids collateral trauma to surrounding tissues, such as would result from open surgery. During such procedures, a surgeon passes instruments through a cannula, manipulates them inside the body through translation and rotation within the cannula, levering the instruments in the body cavity wall and actuating end effectors on the distal end of the instruments. The instruments pivot around centers of motion, defined by the incision.

As used herein, the term "biomaterial" in general refers to a material that is biocompatible, and may be particularly biocompatible for use in tissue engineering as described herein. Such materials can include, but are not limited to, polymer compositions, hydrogels, glasses, metals, ceramics, non-hydrogel polymers, naturally occurring polymers, including collagen and gelatin, and polysaccharides such as glycosaminoglycans. The biomaterial can include an article in different physical forms, such as a membrane, sheet, graft, or mesh. These forms include typical membranes, sheets, grafts, meshes, etc. used in surgery or tissue repair. These articles can include natural products, synthetic products, or combinations thereof. The biomaterial of the present disclosure can be used exclusively to form one of these articles or can be used as a component of one of these articles. "Biomaterial" can be referred to as a "biologic," which refers to a product that may be composed of sugars, proteins, amino acids, or nucleic acids or complex combinations of these substances, or may be living entities such as cells and tissues. "Biomaterial" can also be referred to as a "bioink," which refers to a biocompatible material that includes encapsulated biologics.

As used herein, the terms "hydrogel" or "gel" or "hydrogel matrix" are used interchangeably, and encompass materials including, but not limited to, poly(hyaluronic acid), poly(sodium alginate), poly(ethylene glycol), diacrylate, chitosan, and poly(vinyl alcohol)-based hydrogels. "Hydrogel" or "gel" is also meant to refer to all other hydrogel compositions disclosed herein, including hydrogels that contain polymers, copolymers, terpolymer, and complexed polymer hydrogels, i.e., hydrogels that contain one, two, three, four or more monomeric or multimeric constituent units. Also used herein, the terms "tissue matrix" or "tissue hydrogel" similarly refer to any composition formed into a porous matrix into which cells or tissue can grow in three dimensions. Hydrogels are typically continuous networks of hydrophilic polymers that are capable of absorbing water.

As used herein, the term "growth factor" refers to soluble-secreted signaling polypeptides capable of instructing specific cellular responses in a biological environment. The specific cellular response trigged by growth factor signaling can result in a very wide range of cell actions, including cell survival, and control over migration, differentiation or proliferation of a specific subset of cells. Examples of growth factors include, but are not limited to, angiopoietin, basic fibroblast growth factor, bone morphogenetic protein, epidermal growth factor, fibroblast growth factor, hepatocyte growth factor, insulin-like growth factor, nerve growth factor, platelet-derived growth factor, transforming growth factor, and vascular endothelial growth factor.

As used herein, the term "patient" refers to a human or non-human subject who is being treated, monitored, or the like, for a medical condition, disease or the like, by a healthcare professional.

As used herein, the term "body" refers to the entire structure of a human or non-human subject. The term "body" can also refer to a specific anatomical region of a human or non-human subject.

As used herein, the term "organ" refers to a part or structure of the body, which is adapted for a special function or functions, and includes, but is not limited to, the skin, the lungs, the liver, the kidneys, and the bowel, including the stomach and intestines. In particular, it is contemplated that organs which are particularly susceptible to dysfunction and failure arising from an injury are amendable to tissue-engineered reconstruction and are encompassed by the term "organ." "Tissues" are singular or multiply-layered structures, i.e., monolayers or stratified layers of cells, which are organ constituents. One or more different tissues may form an organ or organs. An organ may also be composed of only one type of tissue or cell, or different tissues or cells.

FIG. 1A illustrates an example printing method 100 of the present disclosure. In various instances, the printing method 100 may be performed within a volume through a small hole (e.g., within a patient through an incision site, such as FIGS. 4 and 5). The small hole may be created using a cannula, knife, or other cutting tool. The printing method 100 includes controlling an end effector 102 to extrude printing material 106 along a printing path 108 with respect to a substrate 104. For example, the end effector 102 may be positioned through the small hole to extrude the printing material 106 on the substrate 104 contained within the volume. The end effector 102 is part of an actuator joint that is mechanically linked to a robotic arm. In various examples, the robotic arm may be a component of a robotic surgery instrument. For instance, the end effector 102 may be a component of the AM device for biomaterials disclosed in U.S. Patent Application Publication No. 2017/0325932, which is herein incorporated by reference. The end effector 102 includes a sharp member from which the printing material 106 is extruded, such as sharp-tipped extrusion needle.

The printing method 100 includes piercing the printing surface 116 of the substrate 104 with the sharp member and extruding a bulb or micro-bolus 110 of printing material 106 beneath the printing surface 116 (e.g., within the substrate 104). The bulb or micro-bolus 110 of printing material 106 is larger than the opening in the substrate 104 created by piercing the printing surface 116 with the sharp member of the end effector 102. The bulb or micro-bolus 110 therefore acts to anchor the printing material 106 to the substrate 104. For example, in tissue implant applications of the printing method 100, the printing method 100 may eliminate the need for sutures to couple the tissue implant to the implantation site of the patient. Each respective bulb or micro-bolus 110 along the printing path 108 may accordingly be referred to as an anchor point. After extruding the bulb or micro-bolus 110, the end effector 102 may be controlled to continue extruding the printing material 106 along the printing path 108 on the printing surface 116. Stated differently, the bulb or micro-bolus 110 beneath the printing surface 116 is continuous with the printing material 106 above the printing surface 116 (e.g., FIG. 1B).

The end effector 102 may be controlled to extrude the printing material 106 along the printing path 108 until another anchor point is reached. Once the next anchor point is reached, the printing method 100 includes piercing the printing surface 116 of the substrate 104 with the sharp member and extruding a bulb or micro-bolus (e.g., the bulb or micro-bolus 114) of printing material 106 beneath the printing surface 116. The end effector 102 may then be controlled to extrude the printing material 106 along the remainder of the printing path 108 while periodically creating anchor points. In some instances, the printing path 108 may terminate with an anchor point.

The substrate 104 may be any structure suitably soft to be pierced by the sharp member of the end effector 102. In some instances, the printing surface 116 of the substrate 104 may be curved or otherwise irregular. In various examples, the substrate 104 may be a patient's soft tissue. In such examples, the substrate 104 may be intracorporeal to a patient, such as one of the patient's organs.

For instance, in such intracorporeal examples, the printing method 100 is part of an endoscopic surgical procedure that enables surgical operations to be performed through "keyhole" incisions. Endoscopic surgical procedures have drastically reduced rates of infection and patient morbidity as compared to open, invasive surgical procedures. When applied to the intracorporeal environment, the printing method 100 accordingly includes making a "keyhole" incision (e.g., with a cannula) through a patient's skin to access the printing surface 116 of the substrate 104 with the end effector 102. The printing material 106 may be therefore be extruded within the patient through the "keyhole" incision.

The example method 100 also includes solidifying the printing material 106. The printing material 106 is a material suitable for extrusion-based AM. Such suitable materials include a composition that behaves like a yield-pseudoplastic fluid ("YPF") such that the printing material 106 inherently partially solidifies after it is extruded. For instance, the printing material 106 may be a gel, hydrogel, paste, slurry, etc. that behaves like a YPF. In some examples, the printing material 106 may be a material that does not inherently behave like a YPF, but is made to behave like a YPF with the addition of rheological modifiers.

The inherent partial solidification described above, however, is not sufficient in most cases to generate sufficient mechanical strength for the final product created by the method 100. In most instances, therefore, the printing material 106 may be solidified via crosslinking techniques. Crosslinking generally refers to the process of forming covalent bonds or relatively short sequences of chemical bonds to join two polymer chains together. When polymer chains are crosslinked, the material becomes more rigid, or solidifies. Crosslinks can be formed in materials by chemical reactions that are initiated by heat, pressure, change in pH, or irradiation. For example, mixing of an unpolymerized or partially polymerized resin with specific chemicals called crosslinking reagents results in a chemical reaction that forms crosslinks. Crosslinking can also be induced in materials that are normally thermoplastic through exposure to a radiation source, such as electron beam exposure, gamma radiation, visible light, or UV light. In general, the longer a crosslinking initiator is applied to the material, the more the material is crosslinked, and the greater the increase in the material's mechanical strength.

In some aspects, the printing material 106 may be extruded and solidified simultaneously. For instance, a crosslinking initiator (e.g., heat, irradiation, or light exposure) may be applied to the printing material 106 as it is extruded out of the end effector 102. As an example, a light source may be directed at the printing surface 116 throughout the printing process. Additionally or alternatively, the crosslinking initiator may be applied (e.g., for less than a minute) to the printing material 106 after the final product is completed. In some instances, the crosslinking initiator may be periodically applied to the printing material 106 throughout the printing process.

In various aspects of the present disclosure, the printing material 106 may be any material suitable for extrusion-based AM, such as plastics (e.g., a thermoplastic polymer) or blends of polymeric binder with metal or ceramic materials. Such materials may be solidified using a suitable crosslinking initiator from any of the above-described crosslinking initiators.

In certain instances, the printing material 106 may be a biomaterial. For example, in tissue engineering applications of the printing method 100, the printing material 106 must be biocompatible so that it may be used within a patient's body. In one aspect, the printing material 106 may be a gelatin methacryloyl ("GelMA") hydrogel. In another example, intracorporeal tissue engineering applications of the printing method 100 have distinct requirements for the printing material 106.

Beyond the standard requirements for a biomaterial, a biomaterial for intracorporeal 3D printing must be capable of being delivered and crosslinked with mechanisms that are safe to native tissues and at physiological temperatures (37° C.) in a wet intracorporeal environment. For instance, the intracorporeal environment is not compatible with UV light, chemical crosslinking, or high temperature methods to solidify the printing material 106. For cell delivery applications, the bioink preparation and delivery method must result in high cell viability. Additionally, the biomaterial and delivery method must enable spatially accurate delivery of biomaterial and the biomaterial must sufficiently adhere or integrate into the native soft tissue.

The printing material 106 must be solidified using a biocompatible crosslinking initiator when extruded in the intracorporeal environment. Excess chemical crosslinking initiator may cause an immune reaction for a patient. Excess UV light exposure may induce DNA damage and tissue aging for a patient; however, the harmful effects from light exposure decrease as the light's wavelength is increased from UV to visible wavelengths. Accordingly, some examples of the printing method 100 include solidifying the printing material 106 by exposing the printing material 106 to light in the visible spectrum (e.g., wavelengths between 400 nm and 700 nm). In at least one example, the printing method 100 includes exposing the printing material 106 to blue light (e.g., a wavelength between 400 nm and 495 nm).

GelMA can be crosslinked using visible light, is biocompatible, exhibits high cell viability, and is biodegradable. GelMA, however, cannot be printed via extrusion-based AM at 37° C. and therefore is not suitable for intracorporeal AM. In various instances, viscofying agents may be blended with GelMA to induce rheological properties in GelMA. In an example, the printing material 106 may be a gelatin methacryloyl ("GelMA") hydrogel blend that includes 7% GelMA, 3% Laponite, and 3% Methylcellulose. For instance, intracorporeal applications of the printing method 100 may utilize the GelMA blend as the printing material 106. The GelMA blend is biocompatible, biodegradable, can be printed via extrusion-based AM, and can be crosslinked via visible light. The GelMA blend also exhibits high cell viability.

In some aspects of the present disclosure, such as tissue engineering applications of the printing method 100, the printing material 106 may include one or more tethered growth factors, cells, drugs, radioactive agents, or radiographic contrast agents. Growth factors, drugs, and cells are often collectively termed biologics. The cells may be any cells appropriate for tissue engineering, such as fibroblasts. In an example, the GelMA hydrogel blend may be mixed with NIH 3T3 fibroblast cells at a concentration of $5.0 \times 10^6$ cell/mL. Such tethered additions to the printing material 106 may serve a variety of tissue engineering functions as will be apparent to one having skill in the art.

As described above, the printing method 100 includes extruding printing material 106 along a printing path 108 while periodically creating anchor points. The printing path 108 may take any form, direction, shape, etc. from a starting point to a terminating point. In some examples, such as illustrated in FIG. 1A, the printing path 108 may alternate back and forth at curved sections 112. It should be appreciated that only one curved section 112 is indicated in FIG. 1A for the sake of clarity. In such examples, the printing method 100 may include creating an anchor point at each respective curved section 112. Stated differently, the printing method 100 may include piercing the printing surface 116 and extruding a respective bulb or micro-bolus 110, 114 at each respective curved section. In some instances, the printing method 100 may terminate after printing a single layer of printing material 106 on the printing surface 116.

Figure 1B:
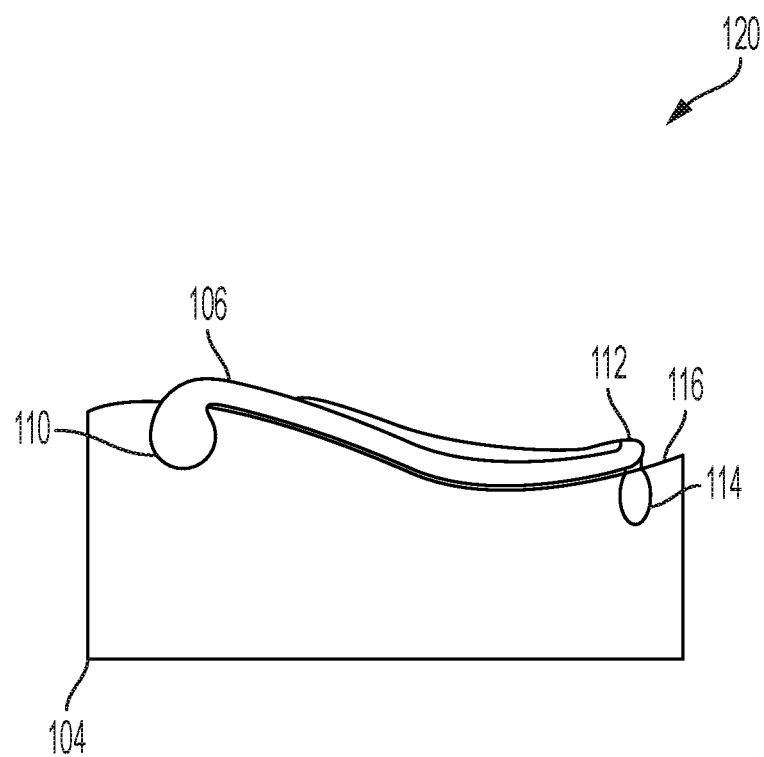
FIG. 1B illustrates a cross-sectional side view of a substrate including a single layer of extruded printing material, according to an aspect of the present disclosure.

FIG. 1B illustrates a cross-sectional side view 120 of the substrate 104 including a single layer of extruded printing material 106. In particular, FIG. 1B illustrates that the bulb or micro-bolus 110 of printing material 106 below the printing surface 116 is continuous with the printing material 106 on the printing surface 116. Similarly, though not illustrated, the bulb or micro-bolus 114 is continuous with the printing material 106 on the printing surface 116 at the curved section 112.

In some aspects of the present disclosure, the printing method 100 described above may include printing a second layer of printing material on top of the first layer. For instance, the printing method 100 may include constructing a mesh from the printing material 106. The printed mesh may be used in place of wherever a surgical mesh or other reinforcing material is currently used in surgical practice. Examples of such meshes that may be printed by the printing method 100 include load-bearing meshes, such as a hiatal hernia mesh, a ventral hernia mesh, an inguinal hernia mesh, an esophagectomy repair mesh, and a sacrocopopexy mesh. The printing method 100 may also create non-load-bearing meshes, such as those used for induced regeneration through stem cell and vascular endothelial growth factor ("VEGF") delivery to compromised native tissue in lobectomies, and mitigation of left ventricular remodeling following myocardial infarction by the delivery of a hydrogel.

Figure 1C:
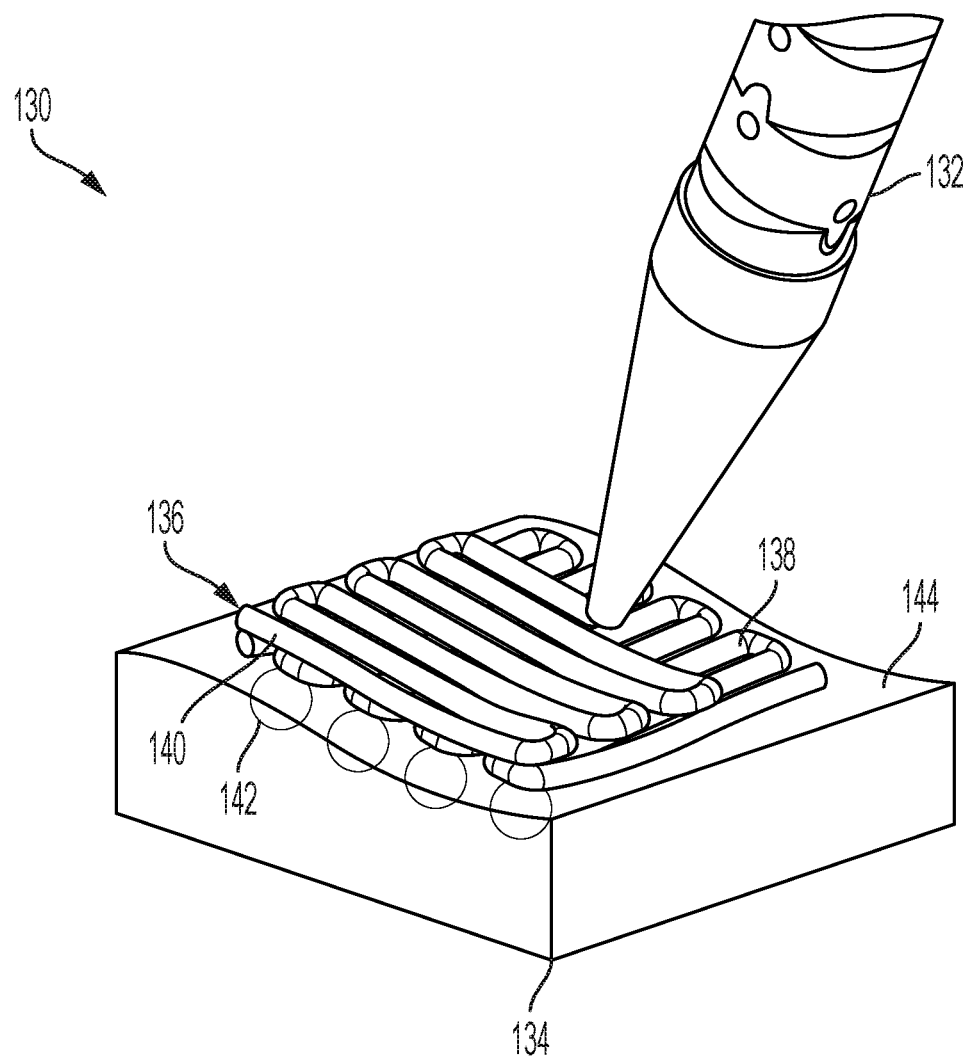
FIG. 1C illustrates an example printing method for constructing a mesh, according to an aspect of the present disclosure.

FIG. 1C illustrates an example printing method 130 for constructing a mesh 136, according to an aspect of the present disclosure. The printing method 130 includes extruding a first layer 138 of printing material on the printing surface 144 of the substrate 134. For instance, the first layer 130 of printing material may be extruded according to the example printing method 100 described above, including periodically piercing the printing surface 144 and extruding a respective bulb or micro-bolus 142 of printing material to create respective anchor points. The printing method 130 then includes extruding a second layer 140 of printing material on the first layer 138 of printing material. In some instances, the printing path is such that the printing material is continuous between the first layer 138 to the second layer 140. In other instances, the printing path is such that the printing material of the first layer 138 is separate from the printing material of the second layer 140. In some aspects, such as the one illustrated in FIG. 1C, the printing path of the first layer 138 of printing material alternates in a first direction, the printing path of the second layer 140 of printing material alternates in a second direction, and the first direction is substantially perpendicular to the second direction. In other aspects, the printing path of the second layer 140 may have other orientations with respect to the first layer 138.

In some aspects of the present disclosure, the presently disclosed AM method may include printing a 3D structure on top of a base printing material layer on a substrate's printing surface. The base printing material layer may be extruded according to the example printing method 100 described above, including periodically piercing the printing surface and extruding a respective bulb or micro-bolus of printing material to create respective anchor points. The 3D structure may then be extruded on top of the base material layer. For instance, the example printing method 100 may include extruding a sequence of layers of printing material, one on top of the other, to create a 3D scaffold, such as a 3D tissue scaffold.

Figure 2:
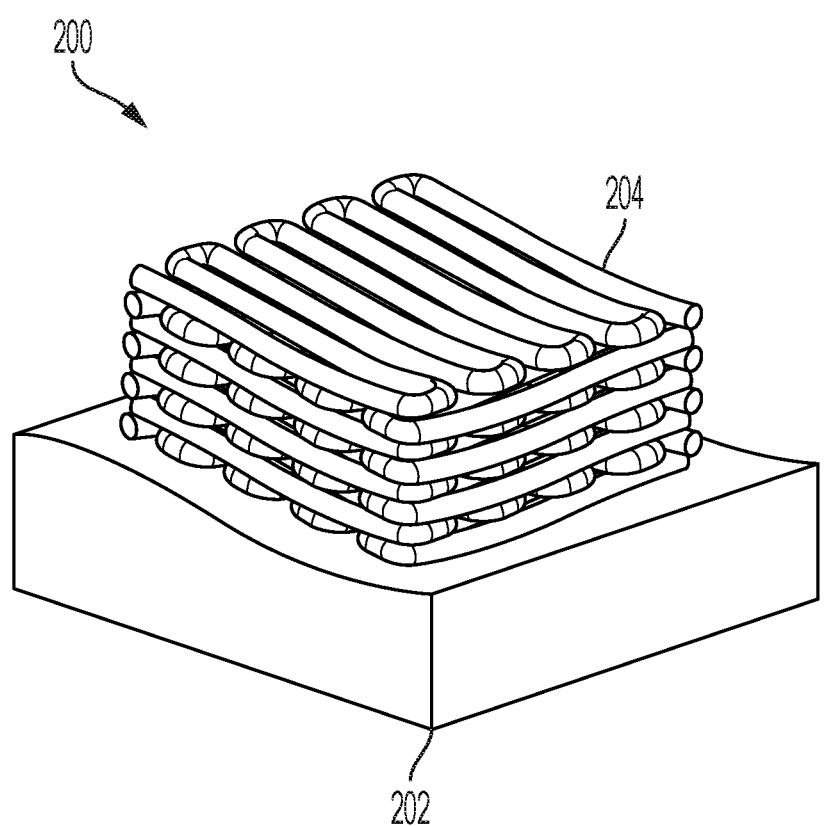
FIG. 2 illustrates an example 3D scaffold of printing material on a substrate, according to an aspect of the present disclosure.

FIG. 2 illustrates an example 3D scaffold 200 of printing material 204 on a substrate 202. In some instances, the printing material 204 may be continuous between each of the material layers in the 3D scaffold 200. In other instances, the printing material 204 of one or more of the material layers in the 3D scaffold 200 may be separate from the other material layers. In some aspects, such as the one illustrated in FIG. 2, the adjacent material layers in the 3D scaffold 200 may alternate orientation in a crisscrossing pattern.

Example 3D structures extruded on top of the base material layer may also include the construction of tubular or membrane-like tissue structures from the printing material. For instance, tubular or membrane-like tissue structures may include replications of parts of a patient's thorax, esophagus, diaphragm, cartilage, cardiac tissue, bladder, sacrocolpopexy creation, stomach wall, vagina, vasculature, nerves, intestine, connective tissue (tendon, ligament, and others), cervix, or uterus. In various examples, 3D structures may be extruded that are not intended to replicate an anatomical feature. For instance, a 3D structure extruded may be an artificial barrier inside a cavity space of a patient, filler material to fill void space of a removed organ, transduction elements for communication with electronically controlled implants. A 3D structure may also be extruded to tether one or more implants. In some instances, a 3D structure may be extruded from the printing material that has dimensions in the x, y, and z directions greater than three millimeters. For example, such 3D structures may include replications of parts of a patient's kidney, liver, bone, muscle, lung, ovaries, or pancreas.

In some aspects of the present disclosure, such as tissue engineering applications, the printing material 204 may include one or more tethered growth factors, cells, drugs, radioactive agents, or radiographic contrast agents. Growth factors, drugs, and cells are often collectively termed biologics. The cells may be any cells appropriate for tissue engineering, such as fibroblasts. In an example, the GelMA hydrogel blend may be mixed with NIH 3T3 fibroblast cells at a concentration of $5.0 \times 10^6$ cell/mL. Such tethered additions to the printing material 204 may serve a variety of tissue engineering functions as will be apparent to one having skill in the art.

The presently disclosed AM method may include constructing structures that include more than one printing material. For example, the 3D scaffold 200 illustrated in FIG. 2 may include some layers of one printing material and some layers of a second, different printing material. The different printing materials may alternate layer by layer or may have any other suitable distribution. Different materials in the same construct may allow for different tissue types or more complex tissue arrangements in the construct. In one example, a precise network of blood vessels may be constructed in a block of soft tissue by printing one material embedded with fibroblasts, and in between that material, printing a sacrificial material containing VEGF and endothelial cells. Blood vessels may then form in the areas there the sacrificial material was printed. In another example, biologics may be precisely delivered at particular locations by printing one material embedded with a first concentration or type of biologic (e.g., cells) and printing a second material with a second concentration or type of biologic (e.g., growth factor).

Figure 3A:
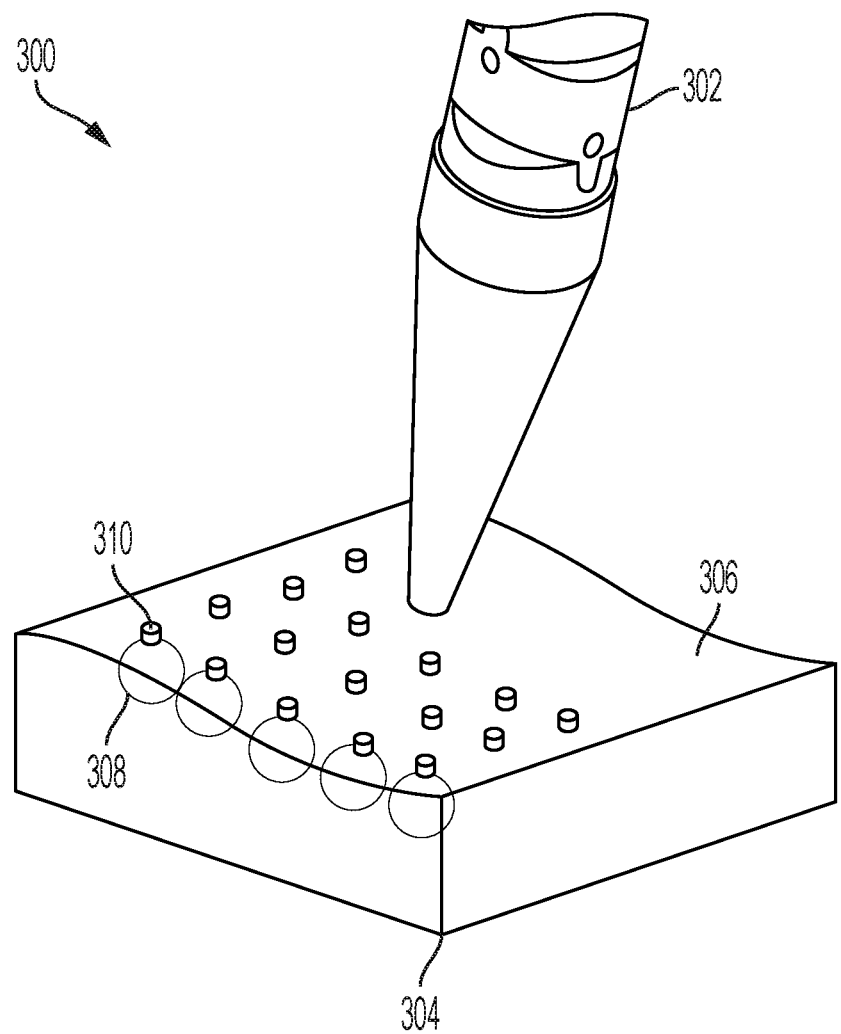
FIG. 3A illustrates an example method for intracorporeal delivery to a patient of biomaterial that includes targeted molecules, according to an aspect of the present disclosure.

In some examples of the present disclosure, the provided AM method may include the delivery of targeted molecules to a patient via a biomaterial. FIG. 3A illustrates an example method 300 for intracorporeal delivery to a patient of biomaterial that includes targeted molecules. The method 300 includes controlling an end effector 302 to pierce a material surface 306 of a substrate 304 and extrude a bulb or micro-bolus 308 of printing material 310 (e.g., a biomaterial) beneath the material surface 306. The printing material 310 includes tethered targeted molecules. The end effector 302 may be consistent with the end effector 102 described above. Additionally, the substrate 304 may be intracorporeal tissue of a patient, as described above in connection with the substrate 104. In some aspects, the method 300 may include extruding a single bulb or micro-bolus 308 of printing material 310. For example, a single bulb or micro-bolus 308 of biomaterial including targeted molecules delivered to a particular location in a patient may be sufficient for the intended purpose of the targeted molecules.

In other aspects, such as the one illustrated in FIG. 3A, the method 300 includes extruding more than one bulb or micro-bolus 308. The end effector 302 is translated between each respective piercing of the printing surface 306 and extrusion of a bulb or micro-bolus 308. In some instances, a portion of a respective bulb or micro-bolus 308 may extend above the printing surface 306, as illustrated in FIG. 3A. The method 300 also includes solidifying the respective bulb or micro-bolus 308 of printing material, as described above in connection with the example method 100.

The target molecules may include one or more tethered growth factors, cells, drugs, radioactive agents, or radiographic contrast agents. Growth factors, drugs, and cells are often collectively termed biologics. The cells may be any cells appropriate for tissue engineering, such as fibroblasts. Such tethered additions to the printing material 106 may serve a variety of tissue engineering functions as will be apparent to one having skill in the art. After a bulb or micro-bolus 308 of printing material 310 is extruded, the bulb or micro-bolus 308 elutes the tethered growth factors, cells, drugs, radioactive agents, or radiographical contrast agents so that the tethered growth factors, cells, drugs, radioactive agents, or radiographical contrast agents do not persist which would otherwise allow the cells to grow and proliferate.

Figure 3B:
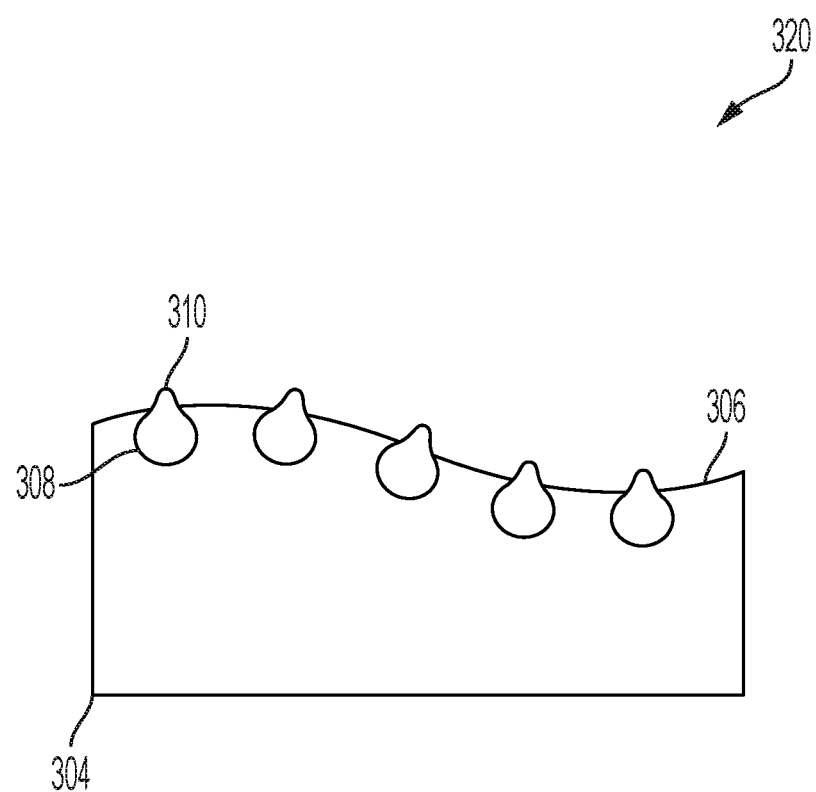
FIG. 3B illustrates a cross-sectional side view of a substrate including multiple bulbs or micro-boluses of extruded printing material, according to an aspect of the present disclosure.

FIG. 3B illustrates a cross-sectional side view 320 of the substrate 304 including multiple bulbs or micro-boluses 308 of extruded printing material 310. In particular, FIG. 3B illustrates that the bulbs or micro-boluses 308 of printing material 310 are below the printing surface 306. Additionally, each respective bulb or micro-bolus 308 may include a portion of printing material 310 that extends above the printing surface 306.

Figure 4:
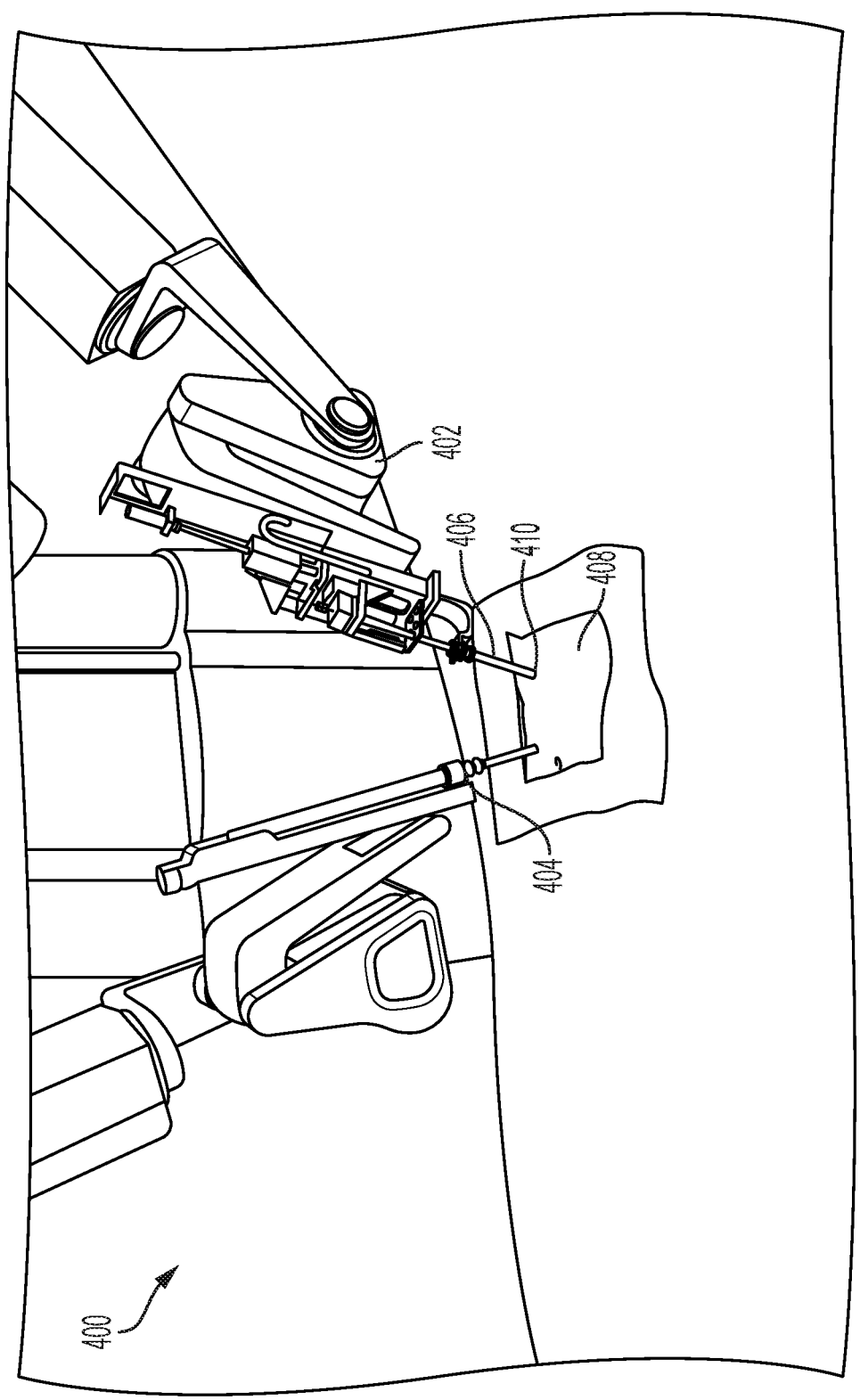
FIG. 4 illustrates a perspective view of a robotic arm utilized to insert an end effector through a keyhole incision site in a patient's skin for freeform extrusion-based additive manufacturing, according to an aspect of the present disclosure.

FIG. 4 illustrates a perspective view of an example method 400 that includes a robotic arm 402 utilized to insert an end effector 406 through a keyhole incision site 410 in a patient's skin 408 for freeform extrusion-based additive manufacturing, according to an aspect of the present disclosure. The end effector 406 may include a number of components that operate together. The end effector 406 is mechanically linked to a joint of the robotic arm 402, which is a component of a robotic surgery instrument. In some examples, the method 400 may include inserting a light source 404 into the patient through a keyhole incision site. The light source 404 provides light within the patient for the surgeon. In various instances, the light source 404 may be a component of the robotic surgery instrument. Typically, the keyhole incision site that the light source 404 is inserted through is separate from the keyhole incision site 410.

Figure 5:
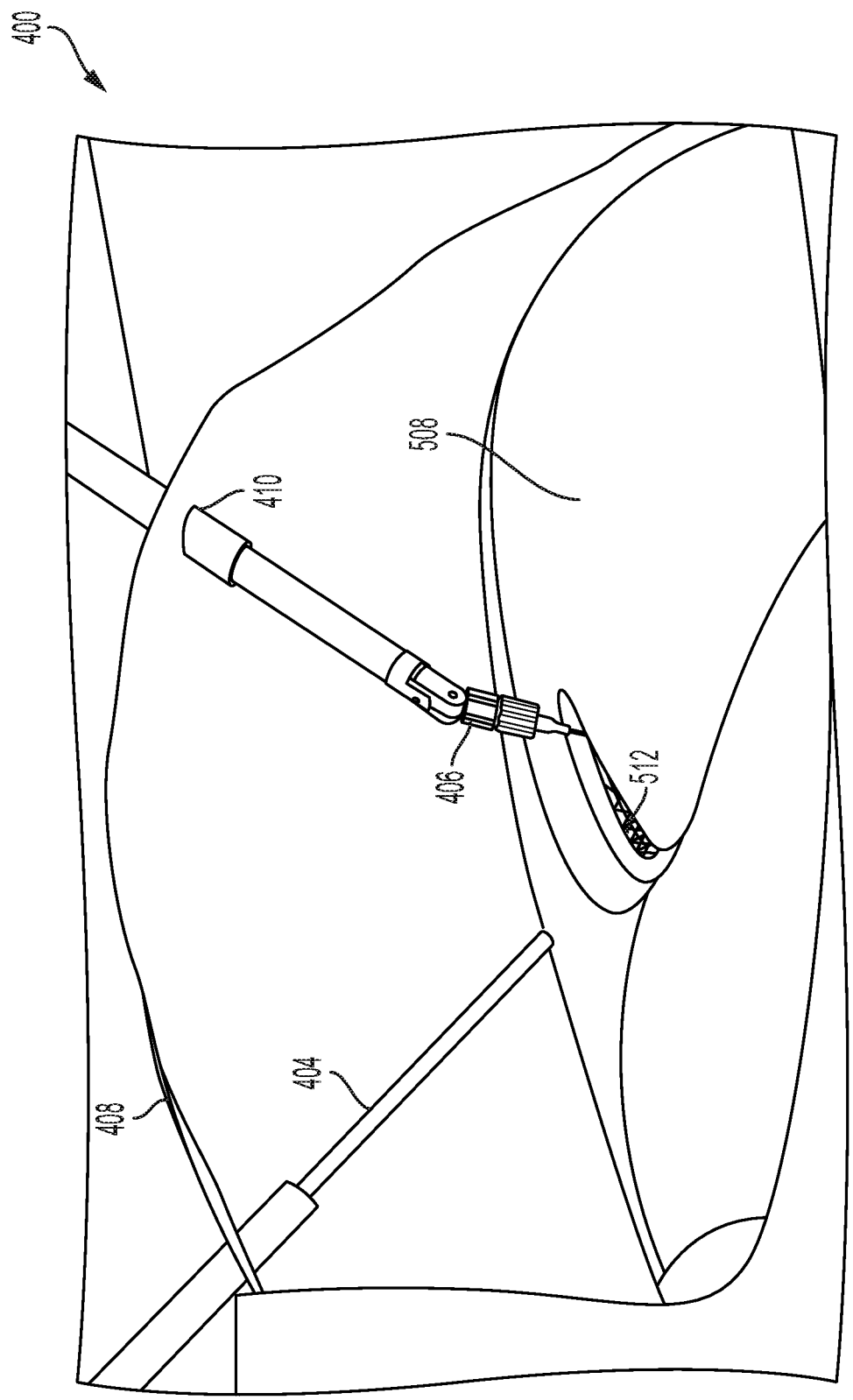
FIG. 5 illustrates a perspective view of the end effector of FIG. 4 printing an example mesh within a patient through the keyhole incision site, according to an aspect of the present disclosure.

FIG. 5 illustrates a perspective view of the example method 400 from within the patient. In this example, the end effector 406 of the robotic arm is additively manufacturing an example mesh 512 within the patient's cavity. The end effector 406 may be inserted through the keyhole incision site 410 made in the patient's skin 408. Once inserted, the end effector 406 may be used to extrude printing material onto a printing surface within the cavity. In this example, the printing surface is the soft tissue of the patient's organ 508. Additionally in this example, the printing material is extruded to form the mesh 512. The light source 404 is also shown through a keyhole incision site in the patient's skin 408.

Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated. The scope of the invention is therefore defined by the following claims.

The invention is claimed as follows:

1. A method for additive manufacturing using an end effector of an actuator joint mechanically linked to a robotic arm, the end effector including a sharp member, the method comprising:
   piercing a printing surface at a first anchor point with the sharp member;
   extruding a first bulb of printing material beneath the printing surface at the first anchor point;
   solidifying the first bulb of printing material;
   extruding printing material along a first printing path on the printing surface;
   solidifying the printing material along the first printing path;
   piercing the printing surface at a second anchor point with the sharp member;
   extruding a second bulb of printing material beneath the printing surface at the second anchor point;
   solidifying the second bulb of printing material;
   extruding printing material along a second printing path on the printing surface;
   solidifying the printing material along the second printing path;
   piercing the printing surface at a third anchor point with the sharp member;
   extruding a third bulb of printing material beneath the printing surface at the third anchor point; and
   solidifying the third bulb of printing material.

2. The method of claim 1, wherein extruding respective printing material and solidifying the respective printing material are simultaneous.

3. The method of claim 1, wherein the printing material partially solidifies as it is extruded.

4. The method of claim 1, wherein solidifying the printing material includes exposing the printing material to light.

5. The method of claim 4, wherein the printing surface is continuously exposed to the light while the printing material is extruded.

6. The method of claim 4, wherein the light has a wavelength in the visible spectrum.

7. The method of claim 6, wherein the light has a wavelength between 400 nm and 495 nm.

8. The method of claim 1, wherein the printing surface is human or animal tissue.

9. The method of claim 1, wherein the printing surface is intracorporeal.

10. The method of claim 1, wherein the printing material is a hydrogel.

11. The method of claim 10, wherein the hydrogel includes 7% gelatin methacryloyl, 3% laponite, and 3% methylcellulose.

12. A method for additive manufacturing using an end effector of an actuator joint mechanically linked to a robotic arm, the end effector including a sharp member, the method comprising:
  extruding printing material along a first printing path on a printing surface to create a first material layer, the first printing path including a plurality of anchor points, wherein creating the first material layer includes:
    piercing the printing surface at each respective anchor point of the plurality of anchor points with the sharp member,
    extruding a respective bulb of printing material beneath the printing surface at each respective anchor point, and
    solidifying each of the respective bulbs of printing material;
  solidifying the first material layer;
  extruding printing material along a second printing path on the first material layer to create a second material layer;
  solidifying the second material layer;
  extruding printing material along a third printing path on the second material layer to create a third material layer; and
  solidifying the third material layer.

13. The method of claim 12, further comprising repeatedly creating a plurality of material layers by extruding printing material along a printing path on each directly preceding layer.

14. The method of claim 13, wherein at least one of the material layers of the plurality of material layers includes a material different than the other material layers of the plurality of material layers.

15. The method of claim 12, wherein the material layers are created in a crisscrossing pattern with respect to adjacent material layers.

16. A method for the delivery of targeted molecules using an end effector of an actuator joint mechanically linked to a robotic arm, the end effector including a sharp member, the method comprising:
  piercing a surface at a first target site with the sharp member;
  extruding a first bulb of a biomaterial beneath the surface at the first target site, wherein the biomaterial includes the targeted molecules;
  solidifying the first bulb of the biomaterial;
  piercing the surface at a second target site different than the first target site with the sharp member;
  extruding a second bulb of the biomaterial beneath the surface at the second target site;
  solidifying the second bulb of the biomaterial; and
  eluting the targeted molecules from each of the first bulb and the second bulb of the biomaterial.

17. The method of claim 16, wherein the targeted molecules include at least one selected from the group consisting of tethered growth factors, cells, drugs, radioactive agents, and radiographic contrast agents.

18. The method of claim 16, further comprising translating the end effector from the first target site to the second target site prior to piercing the surface at the second target site.

19. The method of claim 16, wherein each of the first bulb and the second bulb includes a portion of biomaterial that extends above the surface.

20. The method of claim 16, further comprising repeatedly piercing the surface at a plurality of target sites with the sharp member, extruding a respective bulb of the biomaterial at each respective target site, and solidifying each respective bulb of the biomaterial.

* * * * *